United States Patent [19]
Averback

[11] Patent Number: 5,567,720
[45] Date of Patent: Oct. 22, 1996

[54] PHARMACEUTICALLY ACTIVE AGENTS THAT IMPEDE AMYLOID FORMATION IN VIVO

[75] Inventor: Paul Averback, Montreal, Canada

[73] Assignee: DMS Pharmaceutical Inc., Quebec, Canada

[21] Appl. No.: 265,931

[22] Filed: Jun. 27, 1994

Related U.S. Application Data

[60] Division of Ser. No. 493,276, Jun. 14, 1990, Pat. No. 5,231,170, which is a continuation-in-part of Ser. No. 315,796, Feb. 27, 1989, Pat. No. 4,919,915, which is a continuation of Ser. No. 21,242, Mar. 3, 1987, Pat. No. 4,816,416, which is a continuation-in-part of Ser. No. 901,007, Aug. 27, 1986, abandoned.

[51] Int. Cl.⁶ .................. A61K 31/515; A61K 31/44; A61K 31/35; A61K 31/34

[52] U.S. Cl. .................. 514/345; 514/460; 514/724; 514/407; 514/274; 514/378; 514/379; 514/261; 514/903; 514/883

[58] Field of Search .................. 514/378, 379, 514/274, 407, 724, 460, 345, 261

*Primary Examiner*—Theodore J. Criares
*Attorney, Agent, or Firm*—Foley & Lardner

[57] ABSTRACT

Dense microspheres can be extracted and purified to substantial homogeneity from mammalian brain tissue, and used in the screening of therapies for potential effectiveness in impeding the formation of amyloid fibrils associated with Alzheimer's disease and other forms of cerebral amyloidosis. Compounds that, at in-tissue concentrations of $10^{-5}$ M or less, inhibit amyloid formation in a test animal injected intracerebrally with dense microspheres are particularly useful in inhibiting treating cerebral amyloidosis.

7 Claims, No Drawings

1

PHARMACEUTICALLY ACTIVE AGENTS THAT IMPEDE AMYLOID FORMATION IN VIVO

BACKGROUND OF THE INVENTION

This application is a continuation, division, of application Ser. No. 07/493,276, filed June 14, 1990 now U.S. Pat. 5,231,170, which is a continuation-in-part application based on U.S. Ser. No. 07/315,796 (filed Feb. 27, 1989), now U.S. Pat. No. 4,919,915 which is a continuation of U.S. Ser. No. 07/021,242 (filed Mar. 3, 1987), now U.S. Pat. No. 4,816,416, which in turn is a continuation-in-part of U.S. Ser. No. 06/901,007 (filed Aug, 27, 1986), now abandoned. The respective contents of the aforementioned prior applications are hereby incorporated by reference.

The present invention relates to the identification of compounds that act, at physiologically-compatible levels, to inhibit the formation of proteinaceous tissue deposits denoted generically as "amyloid." More specifically, the present invention relates to pharmaceutically active agents that impede formation of amyloid fibrils in vivo, and to a method for the screening of compounds which possess this activity.

Classified under the rubric "amyloidosis" are a number of pathological conditions characterized by the deposition of abnormal fibrils ("amyloid fibrils") in extracellular spaces. The amyloid fibril, in turn, represents a final common pathway for a diverse array of proteins. Regardless of their biochemical composition, however, all types of amyloid fibrils share (a) a β-pleated sheet structure, (b) green birefringence under polarized light after staining with Congo Red dye, and (c) a fibrillar morphology which has a typical electron-microscopic appearance.

The deposition of amyloid fibrils can affect several organs in the systemic forms of the disorder, exemplified by familial Mediterranean fever, familial amyloid polyneuropathy and systemic amyloidosis, or it can be restricted to one organ in localized forms. Among the latter are conditions classified under the rubric "cerebral amyloidosis," which covers the Alzheimer group of diseases, namely, Alzheimer's disease [pre-senile dementia, senile dementia]; Alzheimer's disease associated with Down's syndrome; Alzheimer's disease associated with other central-nervous-system diseases, such as Parkinson's disorder; and congophilic angiopathy [associated or not associated with Alzheimer's disease].

There is no effective therapy for cerebral amyloidosis, which almost invariably has a fatal outcome following the onset of amyloid deposits. For example, Alzheimer's disease is estimated to be the fourth or fifth leading cause of death among North Americans.

A universally accepted indicator of cerebral amyloidosis is the accumulation of large numbers of lesions, so-called "senile plaques," that are comprised in large part of amyloid fibrils. Senile plaques are spherical, ranging from 10 to 200 μm in diameter, and are found occasionally in aged adult cerebral cortex but in large numbers in Alzheimer-affected cortex.

The utilizing of materials found in human brain (normal or Alzheimer-affected) that are not already amyloid, and of transforming them into amyloid, has not been documented in the literature. There was also no description in the art of an experimental system, derived exclusively from human materials, that was characterized by the feature of Alzheimer's disease. Because the presence of amyloid is the most qualitatively and quantitatively specific indication of senile-plaque formation, most specialists agree that reproduction of amyloid fibrils experimentally from precursor materials which are extracted, activated, or otherwise derived from human brain would constitute the best available evidence linking an agent or precursor to the progression of cerebral amyloidosis.

Despite the recognized importance of an experimental system that would permit testing for such a linkage, it has not been possible to reproduce amyloid experimentally from materials derived solely from human brain tissue. Accordingly, there has been no reliable indicator available for compounds that might be effective in treating cerebral amyloidosis; nor has it been possible to determine whether a group of compounds exists that block the conversion of a brain-localized precursor to cerebral amyloid (i.e., that display "anti-amyloid activity") at physiologically acceptable levels of the active agent.

A microscopic structure referred to as the dense microsphere is known to exist in normal brain and in brain affected by Alzheimer's disease. See Averback, *Acta Neuropathol.* 61: 148-52 (1983); results confirmed by Hara, *J. Neuropath. Exp. Meurol.* (1986). Evidence for the existence of dense microspheres (DMS) comes from microscopic histological section studies of fixed whole brain tissue, where the dense microspheres are seen to have a proteinaceous central region ("DMS protein") surrounded by continuous membrane ("DMS membrane"). The dense microspheres are observed as randomly dispersed, very infrequent structures which occupy an estimated $10^{-9}$ or less of total brain volume, at a unit frequency roughly estimated at $10^{-16}$ or less, relative to other definable brain structures such as mitochondria.

Neither the extraction, purification and characterization of isolated samples of DMS nor the use of DMS material to any advantage has been documented. Thus, DMS are structures of unproven function and unknown significance or usefulness, and have been effectively unavailable in tangible form.

SUMMARY OF THE INVENTION

It is therefore an object of the present invention to provide a method for the screening of therapies for usefulness in impeding amyloid formation and, hence, in treating cerebral amyloidosis, that is characterized by the presence abnormal amounts of amyloid β-protein.

It is also an object of the present invention to provide a method of treating β-amyloid diseases by the administration of a compound selected from a class of pharmaceutically active agents that have in common an ability to inhibit, at physiologically-acceptable levels, the formation of amyloid fibrils in vivo.

It is yet another object of the present invention to provide antibodies that can be used to detect the presence of DMS in biological samples.

It is still another object of the present invention to provide a means for ascertaining whether a given individual is at risk of developing cerebral amyloidosis, even when the individual may not yet have developed clinical symptoms associated with the latter malady.

In accomplishing the foregoing objects, a method has been provided, in accordance with one aspect of the present invention, for treating cerebral amyloidosis, comprising the step of administering to a subject, in whom amyloid formation is anticipated, a pharmaceutically effective amount of a compound that inhibits formation of amyloid fibrils when administered, at an in-tissue concentration of about $10^{-5}$ M or less, to a test animal that has received an intracerebral injection of DMS. In one preferred embodiment, the compound thus administered inhibits amyloid formation by acting on DMS components in such a way that a structural transition of DMS protein in situ to a β-pleated sheet conformation is prevented. The method can be employed where the subject does not display clinical or other evidence indicative of Alzheimer's disease or dementia associated with another disease state, as well as when symptoms of dementia are not evident but the subject tests positive for increased-risk of Alzheimer's disease or dementia due to another disease state. The method can also be administered to prevent a decline in brain function in the subject when the decline is short of dementia.

In accordance with another aspect of the present invention, there has been provided a composition of matter consisting essentially of antibodies, preferably monoclonal antibodies, that are reactive against dense microspheres derived from mammalian brain tissue.

A method has also been provided, in accordance with still another aspect of the present invention, for identifying individuals at risk of suffering cerebral amyloidosis, comprising the step of detecting the presence of a DMS component or an anti-DMS antibody in a biological sample of a mammalian subject, wherein the sample is not derived from brain tissue. In one preferred embodiment, the method comprises the steps of (a) providing antibodies that are reactive with a DMS component, (b) bringing the antibodies into contact with the biological sample and (c) determining whether the antibodies react with the sample. In another preferred embodiment, the method comprises (a) providing a composition comprised of a DMS component or antibody that binds an anti-DMS antibody, (b) bringing that composition into contact with the sample and (c) determining whether the composition is immunologically reactive with the sample.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless otherwise specified, the respective contents of documents cited in the following description are hereby incorporated by reference.

DETAILED DESCRIPTION OF THE PREFERRED EMBODIMENTS

It has now been discovered that the development of amyloid fibrils associated, for example, with the evolution of cerebral amyloidosis is tied to the unchecked disruption of DMS in vivo. The connection between DMS disruption and amyloid formation is evidenced in part by the fact that disrupted DMS treated with Congo Red stain display a red-green congophilic birefringence identical to that found in senile-plaque amyloid. Thus, the most significant aspect of the brain damage which characterizes cerebral amyloidosis can be reproduced using material derived, pursuant to the present invention, from normal mammalian brain samples.

It has also been discovered that compounds which are effective, at a in-tissue concentration of about $10^{-5}$ M or less, in impeding the formation of amyloid fibrils in test animals which receive DMS via intracerebral injection can be used to treat cerebral amyloidosis, including Alzheimer's disease. Particularly effective in this regard are compounds that act on DMS protein or DMS membrane, for example, via intracellular or extracellular binding, so as to prevent a structural transition of DMS protein in the brain to a β-pleated sheet conformation.

The microspheric bodies employed according to the present invention are derived from mammalian brain tissue and are characterized, in essentially homogeneous form, by a range of diameters from about 0.1 μm to about 15 μm, by the above-mentioned outer membrane/proteinaceous core structure of DMS, and by certain stainability properties. (In this regard, "homogeneous" means that the DMS represent the only structure discernible in the subject composition at the light-microscopic level.) For example, the microspheric bodies of the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted, a material is produced that displays congophilic birefringence; that is, when stained with Congo Red the material becomes optically anisotropic to the extent of splitting an incident light wave into two waves with mutually perpendicular vibrational planes.

DMS are spherical, membrane-bounded, intracellular structures, about 0.1 to 15 μm in diameter, that are found in human and other mammalian brains. More specifically, the normal location for DMS is in gray-matter neuropil, where the spherical structures are enclosed in tiny, neuronal cellular processes. DMS are solitary, non-perikaryal and non-confluent, and are not found in cerebellum or in white matter. With regard to inter-DMS distances, the spatial distribution of DMS in gray matter regions is random. Compositions of DMS in homogeneous form can be produced by extraction, according to the present invention, to give homogeneous samples of globular bodies.

The following procedure can be followed to extract DMS from brain tissue:

(1) Whole brain is removed from the skull postmortem, by use of standard postmortem techniques for humans or animals. The best results are obtained if the organism has been in circulatory arrest for less than six hours at the time of brain removal and if the body has been refrigerated as early as possible postmortem. DMS are still extractable at postmortem intervals greater than six hours and are still extractable if body cooling has been delayed or absent, but these two factors will usually greatly decrease the overall average yield of DMS per individual brain. In addition to the effects of post-circulatory arrest interval and temperature on DMS yield, there is considerable individual variation in DMS content per brain, and also individual variation in DMS extractability, which may be related to agonal metabolic state, overall disease status or other factors. All of the factors which determine total DMS yield per brain can have an impact on DMS extraction, since the volume of homogeneous DMS will decrease proportionally to any reduction in percentage extractability; such a decrease may be sufficient to hinder accurate recognition during the extraction procedure. Furthermore, the screening of putative anti-amyloidosis therapies and the characterization of isolated samples of DMS, in accordance with the present invention, are rendered correspondingly more difficult and costly, and ultimately may be impossible at critically small volumes of DMS.

(2) By means of clean instruments, the freshly removed brain is immediately dissected. Dissection is optimally performed in a cold room at 10° C. By means of careful, but rapid, sharp and blunt dissection, the internal capsules, corona radiata, centra semi-ovale, brain stem, cerebellum, lepto and pachymeninges, arachnoid granulations, choroid plexi, and blood vessels are separated and discarded, and the remaining mass of brain is rapidly used for the subsequent steps. (Standard blocks for microscopic study can be removed at this stage and stored separately in histological fixative.) The dissected brain mass ("DBM") is optimally utilized immediately after dissection. It may also be stored frozen at temperatures of −10° C. to −70° C. but this decreases the overall average yield of DMS per individual brain.

(3) The extraction of DMS material from DBM can be carried out by a combination of centrifugation steps. In an exemplary extraction, DBM mechanically homogenized in a 2:1 volume of 0.5 M TRIS-HCl buffer (pH 7.5) is subjected to centrifugation at about 200 rpm for some 10 minutes. (All manipulations are carried out at around 4° C.) The sediment thus obtained ("Sediment I") is separated across a sucrose gradient (1,589 M, or 45%; 1.895 M, or 52%; 2.3895 M, or 62.5%) via centrifugation at 26,000 rpm for 30 minutes. It has been found that the material that settles at the interface between 1,895 M and 2.1015 M (56.7% sucrose)is the DMS-containing fraction, as may be confirmed by microscopic examination, with eosin staining, of the fraction.

The DMS-containing fraction obtained from Sediment I consists essentially of the dense microspheres described above, and can be used in a screening method according to the present invention. It is preferable, however, for the fraction to be subjected to additional manipulations in order to enrich the DMS concentration. To this end, it has proved useful, for example, to wash the DMS-containing fraction in buffer—the above-mentioned homogenization buffer is suitable for this purpose—and to spin the resulting mixture again (10,000 rpm for 7 minutes) to obtain DMS-enriched sediment ("Sediment II").

As with Sediment I, Sediment II can be run through a density gradient to enrich further the yield of DMS. It has been discovered that the carbohydrate Percoll® (Pharmacia) is particularly useful in this context. A commercially available formulation of 80% Percoll® (1.13 g/ml) in 0.15 M NaCl provides a iso-osmolar gradient to which Sediment II can be subjected (30,000 rpm for 15 minutes); successive samples, say, on the order of 0.25 to 1 cc each, can then be taken along the length of the gradient and the DMS-enriched fractions isolated. After these fractions are washed again in buffer, they can be spun down once again (15,000 rpm for 10 minutes) to obtain a sediment ("Sediment III") that is substantially pure DMS.

The DMS materials obtained as described above can be used, pursuant to the present invention, in screening anti-amyloidosis therapies. In particular, homogeneous DMS material within the present invention can be employed to ascertain effectiveness in vitro, on the part of an active agent or a treatment comprising a putative therapy for cerebral amyloidosis, in preventing the red-to green congophilic birefringence that has been found to accompany formation of amyloid when DMS are disrupted.

By whatever means DMS are disrupted in control samples, a putative anti-amyloidosis agent or therapy can be screened by virtue of its ability to retard or preclude amyloid formation under test conditions. For example, in vitro DMS disruption on an appropriate viewing surface, such as a glass or plastic slide (see Test I below), can be accomplished by mechanical means; by the action of an enzyme treatment, as in a 10% trypsin or pepsin solution, or other chemical exposure; or by exposing DMS material to extreme pH values (at room temperature, pH2 or pH10) or temperatures (e.g., 100° C. for one hour). Disruption of DMS can also be effected by injecting DMS material of the present invention into an isolated tissue sample (see Test 2). Brain slices are preferred for this purpose, but liver, pancreas and other organs are also acceptable sources for tissue samples.

An active agent or a treatment that proves effective in-vitro is then tested, pursuant to the present invention, for in vivo efficacy in blocking amyloid-fibril formation in an animal model for cerebral amyloidosis comprised, for example, of a rat, dog, cat or other suitable laboratory animal that has been injected with homogeneous DMS material, pursuant to the present invention. Although intracerebral injection is preferred, injection sites in a test animal's body other than in the brain, such as in skin and in muscle, are suitable for determining the ability of a proposed active agent or treatment step to hinder the resulting formation of amyloid. Because simple injection of DMS onto a glass slide does not result in amyloid formation, it is understood that in vivo production of amyloid fibrils upon injection of DMS occurs in the extracellular spaces of the injected tissue.

According to the present invention, an active agent that impedes in vivo formation of amyloid in DMS-injected test animals, when the agent is present at in-tissue concentrations of $10^{-5}$ M or less, is recognized to be useful in the above-mentioned method of treating cerebral amyloidosis, including Alzheimer's disease. As a further refinement, substances falling within this newly-defined category of pharmaceutically active agents—that is, the class of compounds that, at $\leq 10^{-5}$ M concentration levels in tissues, inhibit induced amyloid formation—can be tested, pursuant to the present invention, in a second in vivo assay.

Particularly preferred for this purpose is the "senile animal" model for cerebral amyloidosis, where animals such as aged dogs or monkeys, which are known to develop variable numbers of Alzheimer-type cerebral senile plaques, see Wisniewski, et al., *J, Neuropathol. & Exp. Neurol.* 32:566 (1973); Selkoe, et al., *Science* 235:873 (1987), are tested for amyloid inhibition. This in vivo assay involves initial pre-treatment- and control-biopsy monitoring to confirm and quantify the presence of senile plaque, and Ser. cerebral biopsy to monitor quantitatively the evolution of DMS and senile plaque in situ and the presence (or absence) of amyloid-formation inhibition.

The method of the present invention for treating cerebral amyloidosis is used with subjects in whom amyloid formation is anticipated. The treatment can be applied, for example, to those who are at risk of developing cerebral amyloid, as in senile plaques, including the elderly, nondemented population and patients with the diagnoses listed above under the cerebral-amyloidosis rubric. In addition to its use in these patient groups, such prophylactic therapy can be effected, pursuant to the present invention, to inhibit or prevent less severe forms of brain-function decline correlated with the formation of smaller amounts of cerebral amyloid in elderly, nondemented subjects in whom dementia, due to the diseases listed above under the cerebral-amyloidosis rubric, is not expected.

Compounds within the present invention that display anti-amyloid activity at an in-tissue concentration of about $10^{-5}$ M or less, e.g., between about $10^{-5}$ and $10^{-6}$ M, can be administered to such subjects orally, rectally, via a nasal route, parenterally (including by skin or other routes), in spray or aerosol form, or via inhalation. A compound within the present invention can thus be administered in a pharmaceutically-acceptable carrier therefore, such as physiological saline solution.

Compounds of the present invention are particularly preferred that, in addition to possessing anti-amyloid activity in the aforementioned concentration range, also are nontoxic at an appropriate dosage level, have an satisfactory duration of effect, and display an adequate ability to cross the blood-brain barrier. In this regard, United States Pat. No. 4,540,564 discloses an approach for enhancing blood-brain barrier-penetrating ability by attaching a centrally acting drug species to a reduced, biooxidizable, lipoidal form of a dihydropyridine⇌pyridinium salt redox carrier. Also particularly preferred are compounds that have specific, selective binding affinity for DMS components.

Determining a pharmaceutically-effective amount of a compound administered in accordance with the present invention entails standard evaluations of pharmacokinetic data and clinical efficacy. See, e.g., GOODMAN AND GILMAN'S THE PHARMACOLOGICAL BASIS FOR THERAPEUTICS (7th ed.). Thus, the above-described in-vivo animal testing will provide the basis for a range of dosages and dosage schedules to be assessed clinically in humans. An assessment in this regard would generate pharmacokinetic data, for example, regarding bioavailability, absorption, metabolism, serum levels and excretion.

Such data would be evaluated against clinical data obtained concurrently from neurobehavioral testing, for example, memory testing and testing of cognitive function, and from clinical medical assessment. If a dosage halts progression of deterioration in clinical parameters for a symptomatic patient, i.e., a subject diagnosed as suffering from cerebral amyloidosis, that dosage should also have a prophylactic effect in the elderly, nondemented population. In addition, a pharmaceutical composition within the present invention could be employed to ameliorate or prevent a decline in brain function, associated with amyloid formation, that is less severe than dementia, e.g., where the subject does not require supervision or nursing care.

Prophylactic therapy in the aforementioned population could be effected, pursuant to the present invention, for all persons of normal brain function who fall within a prescribed age group, for example, 65- or 70- to 75-years old. Alternatively, prophylactic therapy could be applied to non-demented persons of any age who, while displaying normal brain function, are identified via diagnostic testing that reveals evidence of DMS disruption in the brain.

Diagnostic testing of this sort can be conducted by assaying, immunologically or otherwise, for the presence of DMS components such as DMS membrane, DMS protein or fragments thereof in biological samples not derived from brain tissue, e.g., samples of serum, spinal fluid and other bodily fluids. Testing can also be directed to detection in a subject of antibodies against one or more DMS components. In addition, prophylactic therapy according to the present invention can be administered to the nondemented population on the basis of other factors, suggesting a risk for dementia, which are revealed by radiological or diagnostic imaging, genetic testing, electroencephalography or other means.

The following test paradigms illustrate ways in which DMS material, as described above, can be employed routinely, according to the present invention, in identifying anti-amyloidosis agents within the aforementioned class of compounds.

TEST 1

In Vitro Disruption of DMS on a Glass Slide

Homogeneous DMS preparations are placed by droplet on a clean dry glass slide. The volume and number of DMS used is optional but is recommended to be at least several thousand to facilitate interpretation (see Example i below). Larger samples are more costly but are easier and more unequivocal to examine. The DMS are mechanically disrupted using a stainless steel spatula scraping and pressing the DMS against a glass slide in repetitive manual back and forth motions for one minute. The slide is allowed to air dry. A few drops of Congo Red stain are then added to the dried slide and gently passed over the dried disrupted DMS for 30 seconds and the stain is then drained off the slide onto tissue paper or filter paper. The slide is then examined in the light microscope, the latter fitted with crossed polarizing lenses to assess red-green congophilic birefringence.

The result is an unequivocal red-to-green ("apple green") birefringence similar to the red-to-apple green birefringence found in the senile-plaque amyloid of Alzheimer patients, and in quantities proportional to the volume of DMS applied to the slide initially. All other reactions, staining results, or quantitatively insignificant results are considered negative in the absence of the characteristic color change-positive staining result, in quantity proportional to the volume of DMS applied, which indicates that disrupted DMS are of the nature of senile-plaque amyloid.

For test purposes, a corresponding DMS sample is contacted with a possible pharmacological agent, and the DMS disruption/staining procedure as described above is repeated. Many variations are possible, e.g., the active agent may be applied to the DMS in solution, before application to the slide, or to the DMS on the slide. In any event, if the agent prevents the red-green birefringence observed in the negative control slide (no agent present), then the active agent should be tested further for efficacy against cerebral amyloidosis.

As a positive control, the test slide can also be compared to a slide upon which DMS were disrupted after contact with a 1% aqueous solution of sodium diphenyldiazo-bis-α-naphthylamine sulfonate, $C_{32}H_{22}N_6Na_2O_6S_2$; the compound, Congo Red, is described by Graves & Kickham, *New England J. Med*, 214: 782–83 (1936), and Wallace, *The Lancet* (Feb. 20, 1932), at 391–93, and has been found to block amyloid formation in a microsphere-based, in vitro assay according to the present invention.

TEST 2

In Vitro Disruption of DMS in a Human Brain Slice

Human brain postmortem samples of histological block size (block size is elective; usually 1–5 cm×1–5cm×1–3 mm) are removed, by sterile techniques, with the aid of sterile gloves, scalpel and forceps, and then are placed in sterile empty plastic containers, such as a Petri dish before extracted DMS are injected into each brain sample at room temperature. After one hour incubation at room temperature, the brain samples are immersed in histological fixative and processed for histology by techniques that are standard for optical microscopy. Controls, size of inoculum, preparations of slides and interpretation of results are covered under discussion of in vivo Test 3 below.

TEST 3

Formation of Amyloid Induced in Vivo by Injection of DMS Into Live Tissue

Laboratory rodents are anesthetized and their brains immobilized by routine methods, and injections of homogeneous DMS are made into superficial cerebral cortex regions through sterile needles inserted through the skull and meninges. (Sham control injections of DMS negative material can be put into either the contralateral cortex or into separate animals) The method of anesthesia, type of craniotomy, site of injections in the brain parenchyma, size of needle and syringe or other vehicle, wound closure technique, and numbers of animals used are not crucial to the test and will vary depending on the animal used. Thus, a small mouse may not need a skull flap whereas a larger mammal may need a burr hole; size of needles or vehicles may vary with animal brain size, etc. (see Example 1). The size of injection is elective; smaller injections are more difficult and costly to trace histologically (see below), but larger injections are more costly in terms of numbers of DMS used. An exemplary protocol is detailed in Example 1.

The animal is painlessly sacrificed about 30 minutes or more after injection. The exact time of sacrifice is elective; generally, a period of 1 to 24 hours is preferable, but the DMS transformation will persist and can be recognized at many time intervals. After sacrifice the brain is removed by standard methods and immersion fixed in histological fixative. Perfusion fixation is not recommended because perfusion pressures will usually disrupt the injection cavity and render the results inaccessible.

According to standard methods, the brain is fixed in toto for several days (correspondingly longer for larger animal brains), sliced, embedded, cut, mounted and stained for histological study. A dissecting microscope is used to locate the injection site and accurately place it in the block, and sections are carefully inspected during microtomy to ensure that the injection site is in the section and not discarded during trimming. The mounted slides are stained with Congo Red according to standard methodology. The sections are examined with the optical microscope fitted with polarizing lenses as above and assessed as described above with regard to the in vitro test.

The use of positive and negative controls, and the testing of putative active agents, are carried out in a manner analogous to that followed in the in vitro tests described above. Variations are possible by virtue of the fact that compounds can be tested in vivo, via injection, ingestion or other routes, before, after or during the introduction of DMS, and concurrently with or separately from the DMS. In addition, therapeutic strategies other than those based on the action of a pharmacological agent can be studied in whole animals.

By means of the foregoing tests, nontoxic compounds suitable for clinical testing in human beings can be identified, pursuant to the present invention, that impede amyloid formation, preferably by inhibiting the transition of DMS protein to a β-pleated sheet conformation. Because it is immunogenic in standard laboratory animals, the DMS material of the present invention can also be used to produce polyclonal and monoclonal antibodies against dense microspheres. These antibodies, in turn, can be employed in ELISA-type assays, see, e.g., VOLLER, et al., THE ENZYME LINKED IMMUNOSORBENT ASSAY (ELISA) (Dynatech Laboratories 1979), and other immunological tests, such as radioimmunoassays, for detecting DMS in biological samples. Via conventional techniques, as described, for example, by Kennet, et al., *Curr. TOP. Microbiol. Immunol.* 81: 77–91 (1978), anti-DMS antibodies can be produced using the DMS material of the present invention and then "tagged" with a radionuclide, a colorimetric agent or a fluorescent marker. The tagged antibodies can be used in diagnostic tests to detect the presence of components of the dense microspheres with which the antibodies react, rendering the microsphere components visualizable.

In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes and fusing them with myeloma cells, producing hybridomas. The cloned hybridomas are then screened for production of "anti-DMS" antibodies, i.e., antibodies that bind preferentially to a DMS component. "Antibody" also encompasses fragments, like Fab and $F(ab')_2$, of anti-DMS antibodies, and conjugates of such fragments, and so-called "antigen binding proteins" (single-chain antibodies) which are based on anti-DMS antibodies, in accordance, for example, with U.S. Pat. No. 4,704,692.

Alternatively, Mabs or a fragment thereof within the present invention can be produced using conventional procedures via the expression of isolated DNA which codes for variable regions of such an Mab in host cells like *E. coli*, see Ward, et al., *Nature* 341: 544–46 (1989), or transfected murine myeloma cells, see Gillies, et al., *Biotechnol.* 7:799–804 (1989), and Nakatani, et al., *loc, cit,,* 805–10. In addition, Fab molecules can be expressed and assembled in a genetically transformed host like *E. coli*. A lambda vector system is available thus to express a population of Fab's with a potential diversity equal to or exceeding that of subject generating the predecessor antibody. See Huse, et al., *Science* 246: 1275–81 (1989).

Antibodies against DMS components can also be employed in the generation, via conventional methodology, of anti-idiotypic antibodies (antibodies that bind an anti-DMS antibody), e.g., by the use of hybridomas as described above. See, for example, U.S. Pat. No. 4,699,880.

The above-described materials, including DMS components, antibodies to such components, and other molecules, such as stains, that react specifically to indicate the presence of DMS components or anti-DMS antibodies, can thus be employed for the testing of DMS disruption in the brain. Such testing could be used, in accordance with the present invention, in the context of patient-population selection for therapy.

Other details of the present invention are further described by reference to the following illustrative examples.

EXAMPLE 1.

Screening of Acetylcholine for Anti-amyloid Activity in Vitro

Approximately 80,000 homogeneously extracted DMS were placed in a droplet from a Pasteur pipette onto a glass slide, and the droplet was air dried. The DMS adhered to the glass slide. Acetylcholine (20 mM) in physiological saline was added in a droplet, as a possible test compound, to DMS.

The DMS were mechanically disrupted, in the presence of the test compound, as described above and then were allowed to air dry. A control slide was treated exactly in the same manner, except that the test compound was not added. Congo Red stain was added, and the reaction products were examined, as previously described.

Under optical-microscopic examination with a polarizing lens, both slides showed abundant reddish stained material, respectively, in quantities of the order of magnitude as in the initial DMS droplet quantity. The reddish material was observed to turn a brilliant apple green during rotation of the polarizing lens. Rotation of the polarizing lenses back and forth demonstrated unequivocal and abundant red-to-green and green-to-red birefringence which persisted indefinitely. That both slides showed these indistinguishable results meant that acetylcholine had tested negative and, hence, need not be tested further, as described above, to determine whether it belonged to the class of compounds displaying anti-amyloid activity at physiologically-acceptable levels.

EXAMPLE 2.

Illustrative Identification of Compounds, Via an in Vivo Assay, as Effective Amyloid-Formation Inhibitors at Physiologically-Compatible Concentrations In Vivo Assay Male Wistar rats of three-months age were anesthetized by ether inhalation. Their heads are immobilized by means of a stereotactic head brace. Bilateral parieto-occipital scalp incisions (1cm) were made with a sterile scalpel blade. Bilateral parieto-occipital 0.5 mm burr holes are made with a 0.5 mm drill.

For each compound to be assayed (see below), six rats were each injected on one side, through the burr hole from a sterile 1 cc syringe fitted with a sterile 22 gauge needle, with sterile physiological saline containing about 400,000 human DMS and the compound (total volume: 100 μL). The injection was made into the cerebral cortex to a depth of a few millimeters, so that the injection was within the parenchyma, not on the surface or in the ventricles. Consequently, the in-tissue concentration of the compound at the site of injection corresponded to the concentration of the compound in the saline (see tabulated data below).

On the contralateral side, each of the six test rats also received an injection of sterile physiological saline (100 μL). In addition to this internal control, a control group of six rats that did not receive any injection was associated with each test group.

After injection of the test animals, a sterile suture was placed through the scalp incision to cover the wound, and the animals were observed. At post-injection intervals of one hour, twelve hours and twenty-four hours, respectively, four animals (two from the test group and two controls) were painlessly sacrificed by ether inhalation and $CO_2$ insufflation. Their brains were removed and fixed via immersion for twenty-four hours in 10% formalin. The fixed tissue was then sliced coronally, in sections of between 0.5 mm and 1 mm in thickness, and the areas of injection were dissected out and blocked as described above under "Test 3."

The blocks with the injection site were sectioned at a thickness of 6 μm, and every tenth section was mounted to provide a total of ten technically intact sections containing the injection site. The mounted sections were processed and stained with Congo Red, as previously described, and examined, via optical microscopy, with and without polarized illumination. The following measurements were made by means of an optical micrometer and standard counting grids and graticules: (1) total lesion area; (2) total number of foci of congophilic-birefringent amyloid deposits; and (3) percentage of lesion area composed of congophilicbirefringent amyloid deposits.

Tested Compound

An in vitro assay corresponding to Test 1, as described above, indicated that each of the following compounds possessed anti-amyloid activity at a concentration of about $10^{-2}$ M.

(A) Pyrimethamine ("Dataprim")

This compound is conventionally used in the prophylaxis of malaria, and acts by inhibiting dihydrofolate reductase of the malarial plasmodia at a concentration well below the level that inhibits the mammalian enzyme. It is completely absorbed orally and is often used with other drugs in combination therapy. No effects on the central nervous system have been reported for pyrimethamine.

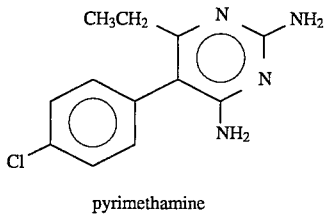

pyrimethamine (B) Dipyridamoe ("Persantine")

The compound, formally designated 2,6-bis-(diethanoi amino) -4,8-dipiperidinopyrimido-(5,4-d)-pyrimidine, is a vasodilator by virtue of its inhibiting the uptake of adenosine by smooth muscle cells. It has no known central-nervous effects.

(C) Nifedipine ("Procardia")

Conventionally employed in cardiac therapy, nifedipine is a dihydropyridine calcium channel blocker that is rapidly and completely absorbed by sublingual administration. It is 98% bound to plasma proteins, and vasodilation is its only major toxic effect. There are no known effects on the central nervous system for this drug.

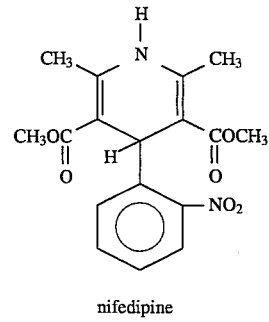

nifedipine (D) Cromolyn Sodium ("Intal")

The known uses of this compound trace to its activity in preventing the release of histamine and other agonists in asthmatic or allergic reactions. It is poorly absorbed orally, with about 10% entering the lungs when the compound is administered, as a powder, from an inhaler. There are no known central-nervous effects.

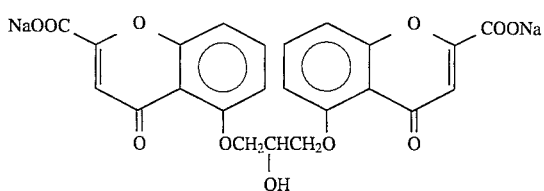

cromolyn sodium (E) Congo Red (Sodium diphenyldiazo-bis-α-naphthylamine sulfonate)

The compound is a dye that has been used as a pH indicator and as a histologic stain, as well as for determination of blood volume and for other diagnostic tests. For example, it is injected intravenously in a test for amyloidosis, whereby 30% of the dye disappears from the blood of a normal person within an hour but 40% to 100% disappears over the same period from a the blood of a victim of amyloid disease. It has had no recognized biological activity per se, however.

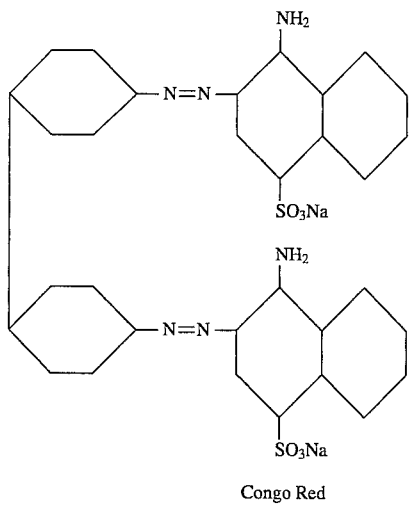

Congo Red (F) Sulfisoxazole ("Gantrisin")

The compound has a good antibacterial spectrum, and is rapidly absorbed and excreted. It binds plasma proteins. Sulfisoxazole has no known effects on the central nervous system, other than antibacterial.

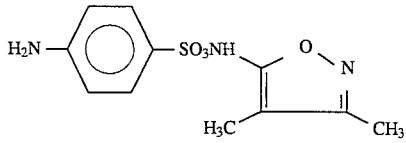

sulfisoxazole (G) Erythromycin

A water-soluble, orally effective antibiotic of the macrolide family, erythromycin inhibits protein synthesis by binding to 50S ribosomal subunits of sensitive microorganisms. It is absorbed by the small intestine and has a half-life of about sixteen hours. The compound has no known central-nervous effects.

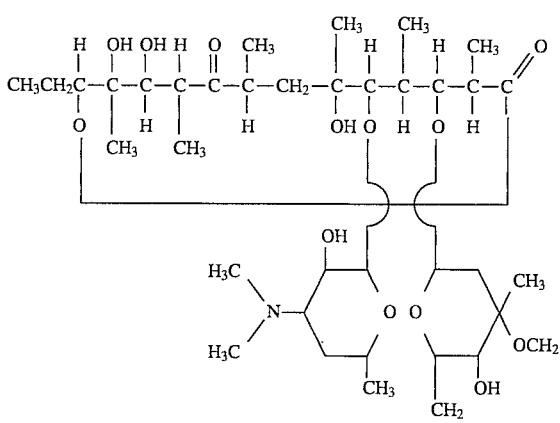

erythromycin

Results

Standard tests for statistically significant differences of means were applied to the above-mentioned measurement data, generated from the brain sections for the six test groups (one group per tested compound) and the corresponding control groups. As shown in the following table, each of the tested compounds effected a significant reduction at $10^{-2}$ M ($p<0.01$). But only three compound, pyrimethamine, cromolyn sodium and erythromycin, were found to inhibit amyloid formation in vivo at in-tissue levels in the range of $10^{-5}$ to $10^{-6}$ M and, hence, to fall in the category of substances suitable for the treatment method of the present invention.

TABLE

| Compound | Mean Lesion Area Examined [mm$^2$] ($10^{-5}$–$10^{-6}$M) | Mean Number of CBADs* Per Animal ($10^{-5}$–$10^{-6}$M) | Mean Lesion Area Composed of CBADs* ($10^{-5}$–$10^{-6}$M) |
|---|---|---|---|
| Daraprim | 10.1 | 4 | 0.2** |
| erythromyan | 12.8 | 2 | 0.2** |
| Intal | 8.9 | 2 | 0.4** |

TABLE-continued

| | Mean Lesion Area Examined [mm²] | | Mean Number of CBADs* Per Animal | | Mean Lesion Area Composed of CBADs* | |
|---|---|---|---|---|---|---|
| | (10⁻²M) | | (10⁻²M) | | (10⁻²M) | |
| Gantrisin | 10.4 | 10.8 | 1 | 108 | 0.1** | 8.4 |
| Persantine | 11.0 | 9.4 | 4 | 146 | 0.2** | 14.6 |
| Procardia | 13.2 | 9.8 | 4 | 88 | 0.2** | 7.6 |
| Congo Red | 12.4 | 10.4 | 1 | 104 | 0.1** | 8.0 |
| <untreated> | | 11.2 | | 132 | | 8.2 |
| | [S.D. 1.2] | | [S.D. 12] | | [S.D. 0.2] | |

*Congophilic Birefringent Amyloid Deposits
**Significant decrease from untreated controls (<0.001)

EXAMPLE 3

Further Identification of Compounds, Via an in Vivo Assay, as Effective Amyloid-Formation Inhibitors at Physiologically-Compatible Concentrations An examination of some five hundred additional compounds, following the procedures set out in Example 1, revealed twenty-seven for which the in vitro assay indicated anti-amyloid activity at a concentration of about $10^{-2}$ M. Several of these were compounds for which the literature suggested a possible utility in ameliorating the effects of Alzheimer's disease, including 2-amino-4-chloro-6-methyl pyrimidine, 4-amino-6-hydroxypyrazolo [3,4-D]pyrimidine, 9-amino-1,2,3,4- tetrahydroacridine hydrochloride (THA), and 2,3-pyridine-dicarboxylic acid. Notably, several other compounds which have been identified previously as beneficially affecting symptoms of Alzheimer's disease, including phytic acid, neostigmine methylsulfate and pyridostigmine bromide, were found not to be active in the in vitro assay, as described in Example 2, even in the $10^{-2}$ -to-$10^{-3}$ M concentration range. Similarly inactive were the compounds trazodone, thioridazine, valproic acid, carbamazepine and trimethophan camsylate ("Arfonad"), all of which have known cerebral effects.

Among the compounds which were found to possess anti-amyloid activity in vitro at about $10^{-2}$ M, only those described below were determined to inhibit amyloid formation in vivo at in-tissue levels in the range of $10^{-5}$ M.

(A) Purpuroqallin

This compound, 2,3,4,6-tetrahydroxy-5H-benzocyclohepten-5-one, has been prepared by oxidation of pyrogallol and has been used heretofore as an additive to oils, edible and inedible, and to hydrocarbon fuels and lubricants, due to its ability to retard oxidation and metal contamination.

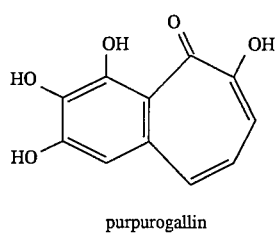

purpurogallin (B) Tartrazine (C.I. Acid Yellow 23) The preparation of this compound is disclosed in U.S. Pat. No. 2,457,823. The compound, which is freely soluble in water, has been used as a dye for wool and silk; it is also FDA-approved for use in food and ingested drugs.

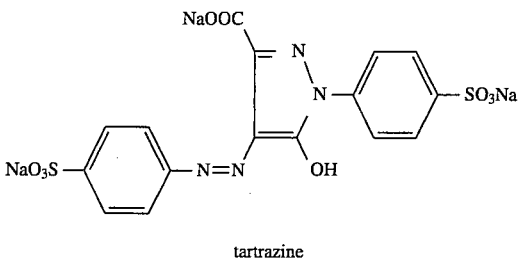

tartrazine (C) Sulfanilamide

Moderately soluble in water, the compound is also soluble in various organic solvents. It is known to have antimicrobial properties.

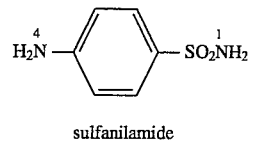

sulfanilamide (D) Benzopurpurine 4B (C.I. Direct Red 2)

The compound, also known as "eclipse red" and "fast scarlet," is prepared from diaxotized o-tolidine and sodium 4-amino-1-naphthalenesulfonate. Used as a dye, primarily for cotton and viscose rayon, the compound is also employed as an analytical reagent in detection of Al, Mg, Hg, Ag and U, and as a biological stain and pH indicator.

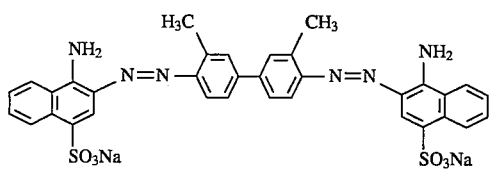

benzopurpurine 4B (E) 29H,31H-Phthalocyanine

This compound has been found to be suitable as a dye, but no biological activity has apparently been attributed to it.

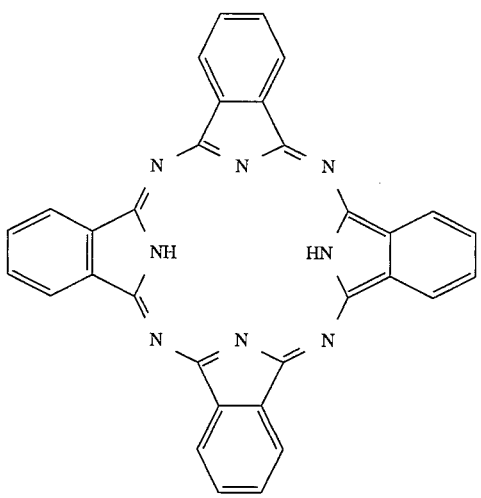

29H, 31H-phthalocyanaine (F) 5-Methyl-2-Thiouridine

The compound is a minor component of tRNA and has been isolated from glutamic acid- and lysine-tRNA's of rat liver. See *Prog. Nucleic Acid Res. Mol. Biol.* 12:49 (1972).

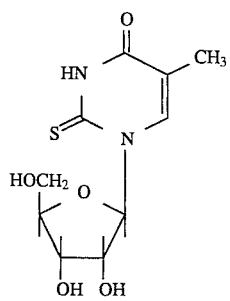

5-methyl-2-thiouridine (G) 1,2-Benzlsoxazole

The compound is light-sensitive but apparently has no known practical utility.

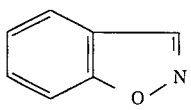

1,2-benzlsoxazole

Compounds that are structural analogues of the in vivo-active agents described above, e.g., compounds carrying one or more substituents differing from those associated with the corresponding agent, are readily prepared and routinely testable, pursuant to the approach described herein, for in vivo efficacy in inhibiting formation of amyloid fibrils.

What is claimed is:

1. A method of treating cerebral amyloidosis, comprising the step of administering to a subject, in whom amyloid formation is anticipated, a pharmaceutically effective amount of a compound that inhibits formation of amyloid fibrils when administered, at an in-tissue concentration of about $10^{-5}$ M or less, to a test animal that has received an intracerebral injection of dense microspheres.

2. A method according to claim 1, wherein said compound inhibits formation of amyloid fibrils by acting on DMS components such that a structural transition of DMS protein in the brain to a β-pleated sheet conformation is prevented.

3. A method according to claim 1, wherein said subject does not display clinical or other evidence indicative of Alzheimer's disease or dementia associated with another disease state.

4. A method according to claim 3, wherein said administering prevents a decline in brain function in said subject, said decline being short of dementia.

5. A method according to claim 1, wherein symptoms of dementia are not evident in said subject but said subject tests positive for increased risk of Alzheimer's disease or dementia due to another disease state.

6. A method according to claim 5, wherein said subject tests positive for presence of DMS disruption in the brain.

7. A method according to claim 1, wherein said compound is selected from the group consisting of pyrimethamine, cromolyn sodium, erythromycin, purpurogallin, tartrazine, sulfanilamide, benzopurpurine 4B, 29H,31H-phthalocyanine, 5-methyl-2-thiouridine and 1,2-benzlsoxazole.

\* \* \* \* \*